US006484791B1

(12) United States Patent
Vidal

(10) Patent No.: US 6,484,791 B1
(45) Date of Patent: *Nov. 26, 2002

(54) PLUNGER FOR A PRESSING FURNACE

(75) Inventor: Patricia E. Vidal, Hillside, NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,121

(22) Filed: Dec. 21, 1999

Related U.S. Application Data

(63) Continuation-in-part of application No. 09/431,659, filed on Nov. 1, 1999, now Pat. No. 6,302,186.

(51) Int. Cl.$^7$ .......................... B22D 17/00; B22D 27/11
(52) U.S. Cl. ......................... 164/113; 164/312; 264/16
(58) Field of Search ................................. 164/113, 312; 264/16, 17; 425/544, DIG. 228

(56) References Cited

U.S. PATENT DOCUMENTS 5,833,464 A   11/1998   Foser
5,897,885 A    4/1999   Petticrew

FOREIGN PATENT DOCUMENTS

EP   0 231 773 A1   12/1997
WO   WO 97/01408    1/1997

*Primary Examiner*—Kuang Y. Lin
(74) *Attorney, Agent, or Firm*—Ann M. Knab

(57) ABSTRACT

A disposable plunger for use in a pressing furnace for the fabrication of dental restorations. The plunger is fabricated of a partially sintered ceramic material. The plunger is fabricated by known casting methods. The mold used for making the plunger can be supplied by a manufacturer of molds or can be easily made by using an alumina or similar plunger as a model. Laborious cleaning and grinding are not required with plungers herein described. Cracking problems that occur with prior art plungers are decreased, if not completely eliminated.

7 Claims, 3 Drawing Sheets

PLUNGER FOR A PRESSING FURNACE

CROSS-REFERENCE TO RELATED APPLICATIONS

This application is a continuation in part application of U.S. patent application Ser. No. 09/431,659 filed on Nov. 1, 1999 now U.S. Pat. No. 6,302,186, which is hereby incorporated by reference.

FIELD OF THE INVENTION

The present invention relates generally to a process of heat pressing of dental restorations and more specifically to a plunger for use in a pressing furnace for transferring pressure from a furnace piston into an investment ring.

BACKGROUND OF THE INVENTION

Dental materials include porcelain facings, veneers, bridges, inlays, crowns, and a multitude of other products. The first step of the casting of, for example, an inlay or a crown, is the preparation of a wax pattern. The cavity is prepared in the tooth and the pattern is carved, either directly in the tooth or on a die that is a reproduction of the tooth and the prepared cavity. If the pattern is made in the tooth itself, it is said to be prepared by the direct technique. If it is prepared on a die, the procedure is called the indirect technique. However the pattern is prepared, it should be an accurate reproduction of the missing tooth structure. The wax pattern forms the outline of the mold into which the alloy or ceramic is cast. Consequently, the casting can be no more accurate than the wax pattern, regardless of the care observed in subsequent procedures. Therefore, the pattern should be well adapted to the prepared cavity, properly carved, and the distortion minimized. After the pattern is removed from the cavity, it is surrounded by a material which forms an investment. This process is called investing the pattern.

Commonly used investment materials include gypsum, phosphate and silica-based materials. Preferably, silica-based investments fabricated from all or a high percentage of quartz or cristobalite are used as dental investment materials. After the investment material has hardened, the wax is eliminated, typically by heat to provide a mold cavity for forming the dental restoration. The investment includes a pouring channel which is formed by a sprue on the wax model. This provides a channel through which the dental materials are supplied to the mold cavity. Dental materials, such as dental ceramics, may be inserted into a premolding space in the form of an unfinished piece or blank. The blank is softened by heat so that it can be introduced into the molding cavity in a viscous state using fairly low pressure to assume the shape of the mold cavity to form the desired dental prosthesis. This process is called heat pressing and is described in "Hot-Compressed Porcelain Process For Ceramo-Metal Restorations" by E. R. McPhee in *Dental Porcelain: The State of the Art*-1977, edited by Henry Yamada, USC School of Dentistry, Los Angeles, Calif. More recently, the process was described in an article by M. J. Cattel et al., entitled "The Biaxial Flexural Strength of Two Pressable Ceramic Systems" in *Journal of Dentistry* 27 (1999) 183–196.

A pressing furnace is used to press the ceramic material into the mold cavity and conform the material to the shape of the cavity. The pressing furnace includes a driving plunger (herein referred to as the "internal plunger") that contacts a second or external plunger inserted into a cylindrical mold which is made from refractory investment. This cylindrical mold is known as an investment ring in the dental field. The external plunger is in contact with the ceramic material. The external plunger transmits the pressing force from the driving plunger to the ceramic material and forces the material through the channel to the cavity. After the pressing operation, the internal plunger is raised, the investment ring and the external plunger are removed from the pressing furnace, and the resultant dental material is removed from the mold. The external plunger must be cleaned after the pressing operation.

In current practice, external plungers are fabricated of a high density alumina. The alumina plungers are intended to be reused for numerous pressings and are relatively expensive. One example of alumina used to manufacture plungers is AD-998 available from Coors Ceramics Company, Golden, Colo. AD-998 comprises 99.8% alumina and has a density of 3.92% gms/cc. It exhibits a flexural strength (MOR) of about 375 MPa (54,000 psi) and a Knoop hardness of 14.1 and a Rockwell hardness of 83 GPa. The coefficient of thermal expansion is $8.2 \times 10^{-6}/°C$. which is generally lower than the coefficient of thermal expansion of the materials to be pressed. Current pressable dental materials have coefficients of thermal expansion in the range of about 17 to about $18 \times 10^{-6}/°C$. for leucite-reinforced materials such as Empress™ material available from Ivoclar, Amherst, N.Y. and OPC® material available from Jeneric/Pentron Inc., Wallingford, Conn. and in the range of about 10 to about 11 for lithium disilicate materials. The plunger must be sufficiently strong and durable to withstand repeated pressings.

Since the external plunger is in direct contact with the ceramic material, it may react or adhere to the ceramic material. Consequently, cracks may form, originating at the interface between the plunger and the ceramic or porcelain button, and propagating through the pressed shape. One reason for this is the difference in shrinkage and cooling rates between the plunger and the ceramic materials used to form the dental restoration. Moreover, if the ceramic materials stick to the plunger, cleaning becomes difficult, rendering reuse inconvenient and problematic. Removal of the glass-ceramic from the plunger requires grinding, sandblasting, and/or soaking the plunger in acid resulting in usage of time and labor which could otherwise be spent on other more constructive tasks. Furthermore, this cleaning process can weaken and distort the plunger reducing the useful life of the plunger. Other techniques have been attempted to solve plunger-related problems, such as modification of the pressing cycle or usage of a massive metal block as a heat sink to promote fast cooling of the ring in an effort to avoid cracking. Nevertheless, these solutions have not been proven to be fully effective and cracking may still occur from time to time.

There is a need to reduce or eliminate time involved in cleaning the external plunger after completion of the pressing operation. It is desirable that cracking problems occurring during the pressing operation be reduced or eliminated.

SUMMARY OF THE INVENTION

These and other objects and advantages are accomplished by the invention comprising a disposable external plunger for a pressing furnace. The plunger is fabricated of a partially sintered ceramic material. The partially sintered material is not sintered to full density. The strength of the partially sintered material may be at least about 3 MPa and not exceed 20 MPa.

Examples of partially sintered refractory materials include refractory materials which can be further delineated to castable refractory materials. Refractory investment materials is a further subclass which can be used in the manufacture of the plungers herein described.

Refractory investment materials useful herein include gypsum and phosphate-bonded investment materials which comprise a filler material such as silica materials, for example, quartz or cristobalite or a combination thereof. The plunger is fabricated by known casting methods. The mold used for making the plunger can be supplied by a manufacturer of molds or can be easily made by using an alumina or similar plunger as a model.

As an alternate embodiment herein, the plunger may be fabricated of an unfired ceramic material in the form of a green body. The green body has a sufficient green strength to withstand handling. The "green" plunger is partially sintered in the premolding phase of the pressing operation providing strength sufficient for pressing the pellet material in the fabrication of dental restorations.

The plunger herein provides an efficient and effective way to alleviate problems associated with prior art plungers. It is inexpensive and simple to manufacture and therefore can be disposed of after use. Laborious cleaning and grinding are not required with plungers herein described. Cracking problems that occur with prior art plungers are decreased, if not completely eliminated.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
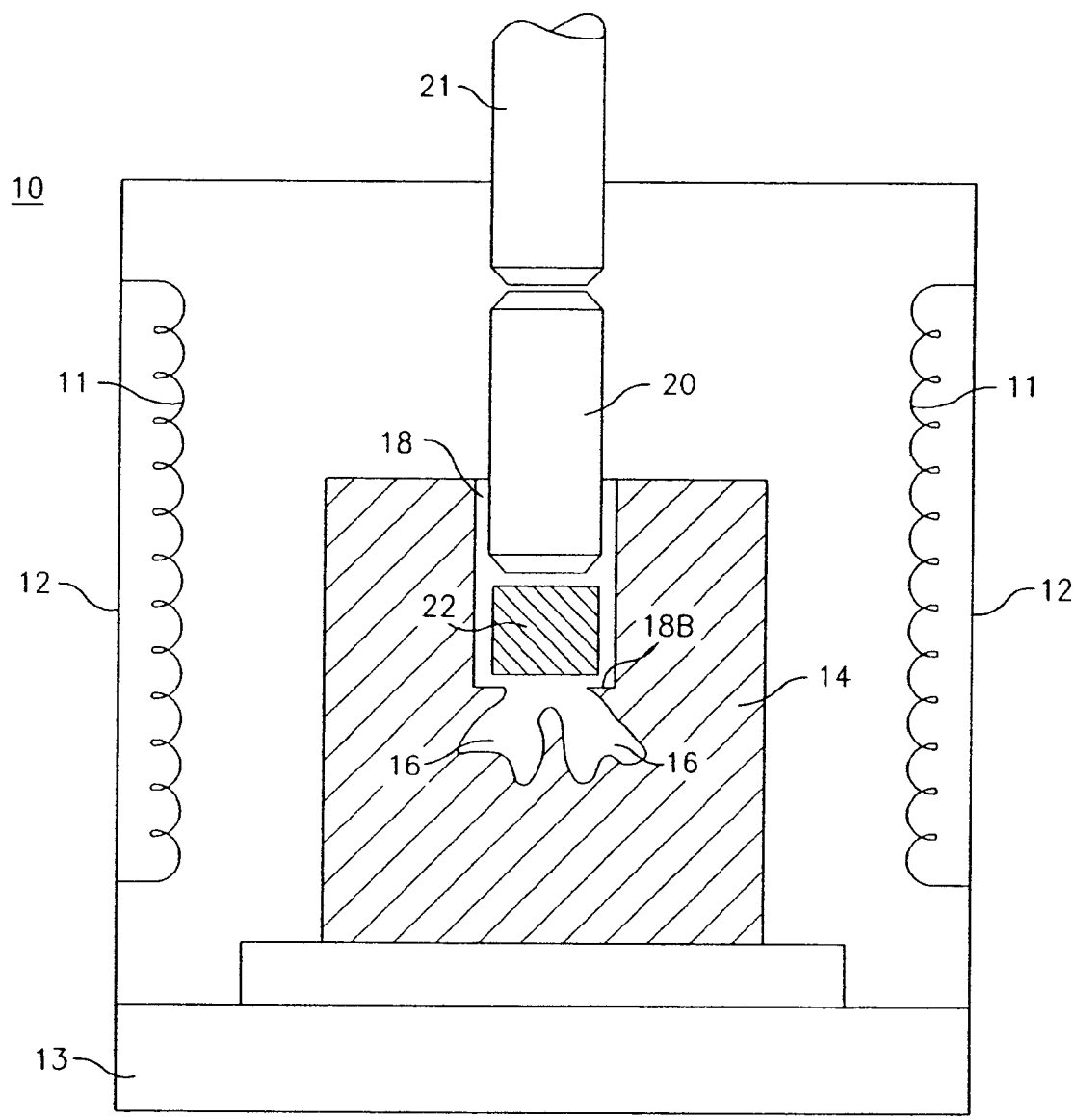
FIG. 1 shows a partial elevational view of a pressing furnace showing the plunger of the invention in pressing position.

As will be appreciated, the invention provides a plunger for use as an external plunger in a pressing furnace used in the manufacture of dental restorations. FIG. 1 is a partial view of a pressing furnace 10 having heating coils 11 disposed proximate walls 12. A pressing or firing platform 13 for holding an investment ring 14 is located at the bottom of furnace 10. Investment ring is an industry term for a cylindrical mold made from a refractory investment material. Investment ring-type materials are disclosed in U.S. Pat. No. 4,478,641 to Adair et al., which is hereby incorporated by reference. Investment ring 14 is formed by known methods around a wax pattern. The wax pattern is then eliminated by heat to provide mold cavity 16. A premolding space 18 is also formed in investment ring 14. An external plunger or piston rod 20 is located in premolding space 18. An internal piston or plunger 21 is positioned above external plunger 20 in furnace 10. External plunger 20 has approximately the same diameter as internal piston 21 of about 12 mm. During the pressing operation, plunger 20 is pushed down to the bottom wall 18B of premolding space 18 by plunger 21. As plunger 20 is pushed down, a blank or pellet 22 is forced into mold cavity 16. The blank is made of a glass-ceramic or porcelain material. Commercially available glass-ceramic materials in the form of blanks or pellets include leucite based glass-ceramic materials, sometimes referred to as high strength feldspathic porcelains such as OPC® pellets from Jeneric/Pentron, Inc. and Empress™ pellets available from Ivoclar, and lithium disilicate based glass ceramic materials such as Empress™ 2 available from Ivoclar.

Plunger 20 is fabricated of a partially sintered ceramic material. The partially sintered material is not sintered to full density. The strength of the partially sintered material may be at least about 3 MPa and not exceed 20 MPa.

Examples of partially sintered refractory materials include refractory materials which may include castable refractory materials and investment refractory materials.

Investment refractory materials useful herein include gypsum-bonded, phosphate-bonded or ethyl silicate-bonded investment materials. These investment materials normally contain up to 80% of a refractory filler such as quartz, cristobolite, other forms of silica, leucite or mixtures thereof. These investment materials are commercially available and are widely used in dental laboratories for various purposes. Examples of commercially available investment materials include RapidVest® investment available from Jeneric®/Pentron® Inc., Wallingford, Conn.; Accu-Press™ investment available from Talladium Inc., Valencia, Calif.; PC15™ investment available from WhipMix Corporation, Louisville, Ky.; and Speed™ investment available from Ivoclar North America, Amherst, N.Y.

Examples of castable refractory materials include high temperature melting and casting materials which you can cast and use as a refractory such as Ceramacast™ brand castable refractory materials from Aremco Products Inc. (Ossining, N.Y.). Ceramacast castables comprise a mixture of a filler and a bonding agent whereby the filler is based on alumina, zirconia, magnesia, zircon, aluminosilicate, cordierite, mica, and mixtures thereof.

As an alternate embodiment herein, the plunger may be fabricated of an unfired ceramic material in the form of a green body. The green body has sufficient green strength to withstand handling. The "green" plunger is partially sintered in the premolding phase of the pressing operation providing strength sufficient for pressing the pellet material in the fabrication of dental restorations.

Plunger 20 is fabricated by known casting methods such as for example, by casting investment or other material in a rubber mold. Plunger 20 is strong enough after the burn-out procedure to withstand pressing at temperatures from about 900° C. to about 1200° C. and pressures of up to about 7 atm. Normally, pressure of about 5 to about 6 atm is sufficient to cause viscous flow of heated glass-ceramic into the cavity of the mold. The mold used for making plunger 20 can be supplied by a manufacturer of molds or can be easily made by using an alumina or similar plunger as a model. Ten plungers can be cast from one 100 gram bag of investment.

The technique described herein is often referred to as injection molding of dental glass-ceramics. It is indeed close to injection molding of plastics and metal injection molding since the glass-ceramic pellet heated to the temperature of pressing attains sufficiently low viscosity to flow in the cavity under pressure normally not exceeding 0.7 MPa. The corresponding stress developed in the cross-section of the plunger during its uniaxial loading through the internal piston of the same diameter is less than about 1 MPa.

Plunger 20 is easily fabricated of a partially sintered ceramic material and provides an efficient and effective way to alleviate problems associated with prior art plungers. It is inexpensive and simple to manufacture and therefore can be disposed of after use. Laborious cleaning and grinding are not required with plungers herein described. Cracking problems that occur with prior art plungers are decreased, if not completely eliminated.

It is important to note that the partially sintered ceramic material used to make plunger 20 exhibits a thermal expansion higher than that of pressable pellet 22. This is important during the cooling phase of the pressing operation, because plunger 20 shrinks faster than the material of pellet 22. The higher thermal expansion of the material of plunger 20 with respect to the thermal expansion of the material of pellet 22 prevents thermal expansion mismatch cracks from originating and further propagating through the restoration pressed from pellet 22. In non-disposable plungers currently used, crack propagation problems exist because the thermal expansion of the non-disposable plunger material (e.g., high density alumina) is lower than that of the pellet material.

The disposable plungers herein exhibit a modulus of rupture (MOR), also known as flexural strength, in the range of about 3 to about 20 MPa. This quantifies the range of strengths required for the plunger to be strong enough to withstand pressing parameters involved in fabricating dental materials and also to be sufficiently weak to facilitate its removal and disposal after pressing.

The methods and materials for mass production of disposable plungers herein described can include any and all ceramic materials and methods to produce plungers which are cheap and weak enough to be easily disposed of. Examples of these forming methods conducive for mass-production of ceramic parts and components include casting, slip-casting, extrusion and dry-pressing. In most cases, green parts produced by these techniques should be partially sintered to impart strength of at least about 3 MPa and not exceeding about 20 MPa. This is easily achieved by selecting the appropriate firing temperature.

Optionally, the green parts may be used as plungers and will be partially sintered during the premolding phase of the pressing operation since the plunger is inserted into a burn-out furnace and then transferred into the pressing furnace prior to initiating start-up of the operation. Depending upon the material used to be pressed, the burn-out furnace is preheated to a temperature in the range of about 760 to about 950° C. During this preheating stage, the plunger in its green state, will be partially sintered to provide a sufficiently strong plunger which can be used during pressing. The plunger may be additionally sintered in a burn-out furnace during the necessary pre-heat step since using a cold plunger is not recommended.

Figure 2:
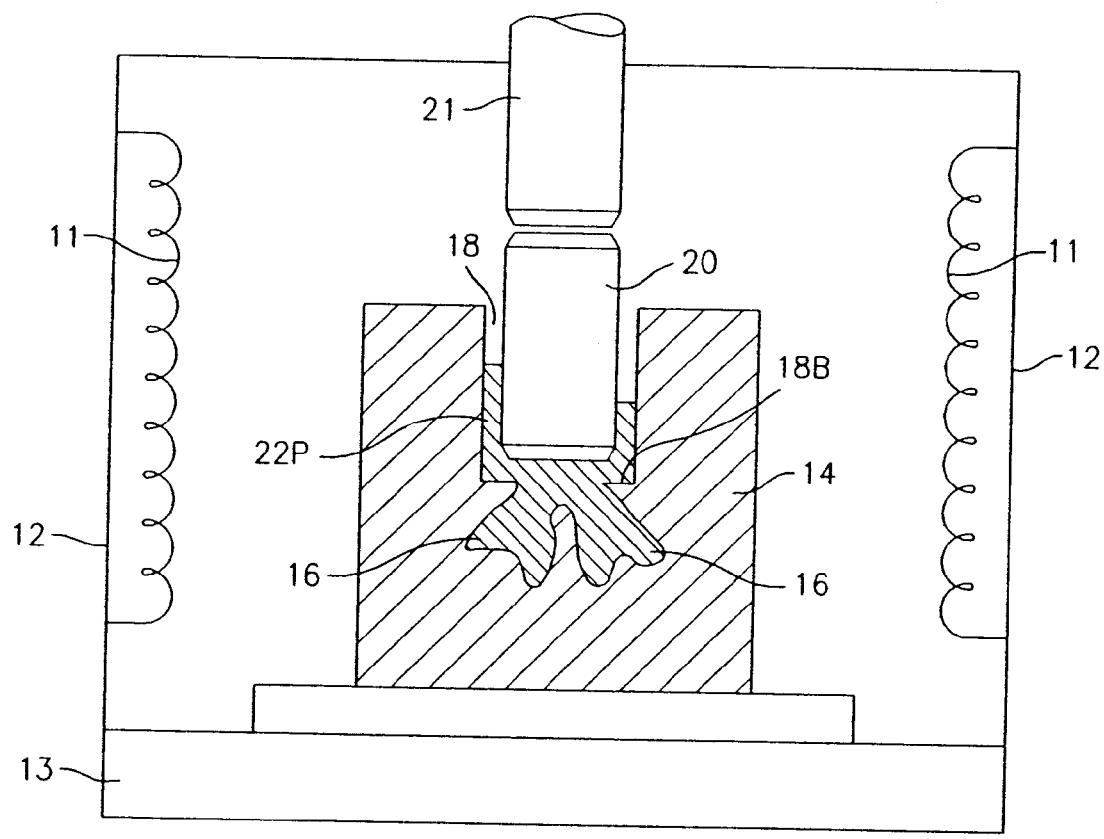
FIG. 2 shows a partial elevational view of a pressing furnace showing the plunger of the invention after pressing has taken place.
Figure 3:
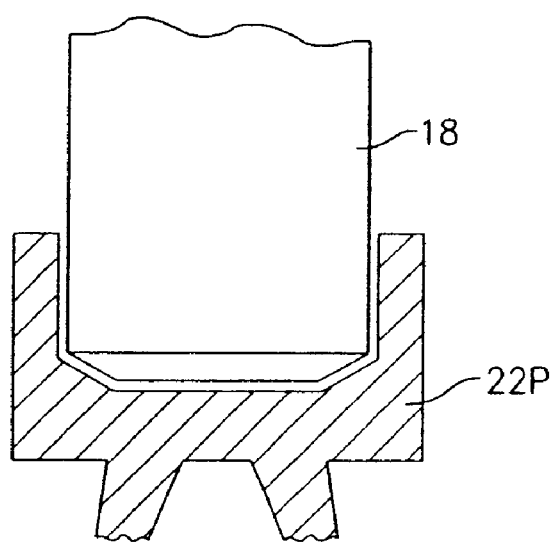
FIG. 3 is a sectional schematic view of the plunger of the invention and the pressed material after pressing has taken place.

FIG. 2 shows plunger 18 in position after pressing has taken place. The temperature in the furnace in combination with the pressure from plunger 18 forces pellet 22 to flow into cavity 16 and form pressed pellet material 22P. FIG. 3 is a schematic diagram of plunger 18 after pressing has taken place with respect to pressed pellet material 22P. Due to the higher thermal expansion of plunger 18 with respect to the thermal expansion of pellet material 22, plunger 18 may shrink away from the pressed material, making it easier to remove it from the pressed piece. Preferably, the thermal expansion of the plunger material is about $0.3 \times 10^{-6}/°C$. units greater than the thermal expansion of the dental material.

Figure 4:
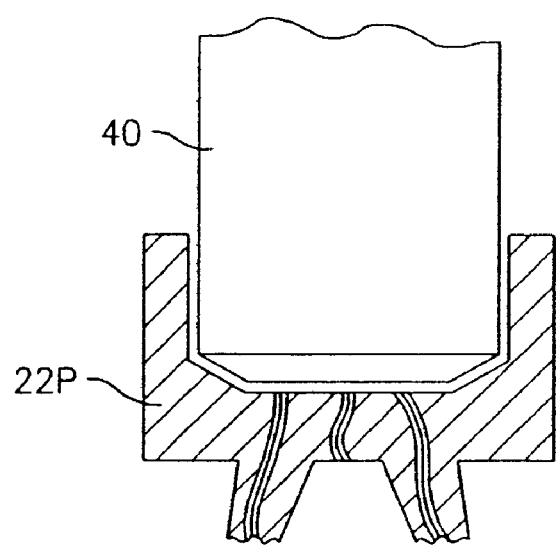
FIG. 4 is a sectional schematic view of a prior art plunger and pressed material after pressing has taken place.

FIG. 4 shows a prior art plunger 40 fabricated of fully sintered high density alumina after pressing has taken place.

Pressed pellet material 22P shows cracks thereon which are a result of the thermal expansion rates of the pressed pellet material 22P being higher than the alumina of plunger 40. In addition to cracks forming, pressed pellet material 22P has reacted with plunger 40 and is partly fused to plunger 40. The cracks may extend to the actual pressed dental restoration which render it unusable. If the cracks do not extend to the actual restoration, the restoration may be usable, but plunger 40 will have to be removed from the furnace and cleaned to remove all traces of pellet material 22P so that it can be reused. In comparison to plunger 18 in FIG. 3, plunger 18 may be removed and disposed of without expending time and energy on trying to remove pellet material therefrom.

The following example illustrates the practice of the invention.

EXAMPLE

An external alumina plunger currently used with the AutoPress® furnace available from Jeneric®/Pentron® Inc., Wallingford, Conn. was used as a model to fabricate rubber molds. Four different refractory silica-containing phosphate bonding investment materials were used to make disposable plungers: (1) RapidVest® investment available from Jeneric®/Pentron® Inc., Wallingford, Conn.; (2) Accu-Press™ investment available from Talladium Inc., Valencia, Calif.; (3) PC15™ investment available from WhipMix Corporation, Louisville, Ky.; and (4) Speed™ investment available from Ivoclar North America, Amherst, N.Y. The four materials were mixed with a colloidal silica solution and water as recommended by the manufacturer for the making of investment rings. Distilled water can be used instead of the colloidal silica solution.

The investment mixture was poured into molds and the cast plungers were bench-set and burned-out similar to the process used in the manufacture of refractory rings. The disposable plungers were then ready for use. The plungers were used to press OPC® porcelain pellets available from Jeneric®/Pentron® Inc., Wallingford, Conn., at 1175° C. and LACS pellets (new experimental lithium disilicate pressable ceramics) at 910° C. to 920° C. in an AutoPress® furnace. The plungers were removed thereafter and disposed of. No cracks were present in the porcelain button, sprue or coping. The plungers that were in the burnout oven, but were not used to press any pellets, were removed from the burn-out furnace and used at a later time without noticeable deterioration of strength.

As will be appreciated, the present invention provides a fast and efficient method of pressing dental restorations. A disposable plunger reduces and/or eliminates cracking problems associated with prior art plungers. Cleaning and grinding of plungers are eliminated by the disposable plunger herein described.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. Method of making a dental restoration using a pressing furnace comprising:

pushing an internal plunger onto an external plunger whereby the external plunger contacts a dental ceramic material and forces the dental ceramic material to flow into a mold cavity space to form the dental restoration;

raising the internal plunger; and removing the external plunger from the pressing furnace and disposing of the external plunger;

whereby the external plunger is fabricated of a second ceramic material having a coefficient of thermal expansion higher than the coefficient of thermal expansion of the dental ceramic material.

2. The method of claim 1 whereby the external plunger has a flexural strength in the range of about 3 to about 20 MPa.

3. The method of claim 1 whereby the second ceramic material comprises a material that is not fully densified.

4. The method of claim 1 whereby the mold cavity comprises an investment ring and wherein the external plunger and the investment ring are fabricated of the same material.

5. The method of claim 1 whereby the second ceramic material comprises a partially sintered ceramic material.

6. The method of claim 1 whereby the second ceramic material comprises a castable refractory material.

7. The method of claim 1 whereby the second ceramic material comprises an investment refractory material.

* * * * *